United States Patent [19]

Breslau

[11] 4,266,026
[45] May 5, 1981

[54] CATALYTIC PROCESS UTILIZING HOLLOW FIBER MEMBRANES

[75] Inventor: Barry R. Breslau, Acton, Mass.

[73] Assignee: Rohm and Haas Company, Philadelphia, Pa.

[21] Appl. No.: 776,339

[22] Filed: Mar. 10, 1977

Related U.S. Application Data

[63] Continuation-in-part of Ser. No. 601,959, Aug. 4, 1975, abandoned.

[51] Int. Cl.³ .................. C07G 7/02; B01D 13/00
[52] U.S. Cl. .................. 435/99; 435/182; 435/288; 426/41; 210/632; 210/638
[58] Field of Search .......... 195/63, 68, DIG. 11; 210/22, 23 F, 321 D, 321 K; 435/99, 182, 288; 426/41

[56] References Cited

U.S. PATENT DOCUMENTS 3,809,613  5/1974  Vieth et al. .................. 195/68 X

OTHER PUBLICATIONS

Immobilized Enzymes, O. R. Zaborsky, CRC Press, 1973, pp. 104–115.
Dinelli, "Fibre Entrapped Enzymes", from *Process Biochemistry*, Aug. 1972, pp. 9–12.

Primary Examiner—Frank A. Spear, Jr.
Attorney, Agent, or Firm—Louis F. Kline, Jr.

[57] ABSTRACT

Catalysts of various types, preferably enzymes, are immobilized on hollow fiber membranes in novel way to provide a new system for performing catalytic reactions. In preferred embodiments, novel processes for catalyzing reactions utilizing hollow fiber techniques are disclosed.

9 Claims, 8 Drawing Figures

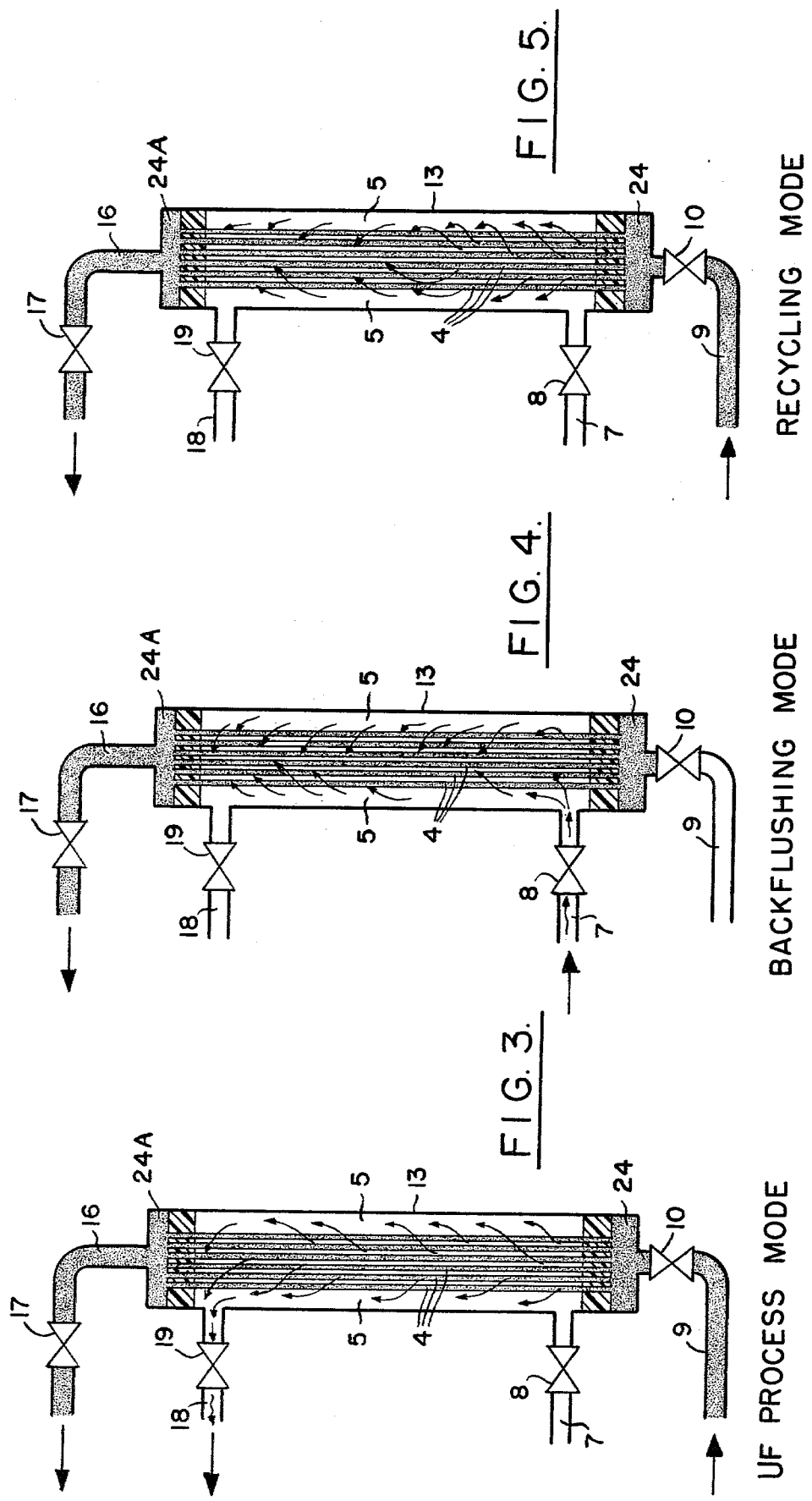

CATALYTIC PROCESS UTILIZING HOLLOW FIBER MEMBRANES

This application is a continuation-in-part of my co-pending U.S. patent application Ser. No. 601,959 filed Aug. 4, 1975, now abandoned.

BACKGROUND OF THE INVENTION

This invention relates to anisotropic hollow fiber membranes having immobilized thereon catalysts, preferably biological catalysts, and methods of using such membranes to perform catalytic reactions. Alternative methods also provide for ultrafiltration of a substrate solution while concurrently providing for the catalytic reaction of the substrate.

Hollow fiber membranes have heretofore found widespread use in the fields of ultrafiltration, reverse osmosis, and related separation processes. Ultrafiltration is a process of separation whereby a solution, containing a solute of molecular dimension significantly greater than the molecular dimensions of the solvent in which it is dissolved, is depleted of the solute by being subject to such pressure that the solvent is forced to flow through a membrane. "Ultrafiltration" is the term preferably used to describe such pressure-activated separations involving solutions of solutes of from about 500 molecular weight and above; the term is also conveniently used for processes involving, instead of dissolved molecules, colloidal-sized particles.

"Reverse osmosis" is a term conveniently reserved for membrane-separation processes wherein smaller molecules are involved, for example those molecules or solids which are of a size within one order of magnitude of those of the solvent.

The particular advantages of such membrane-modulated separation processes as described above lie in their potential speed, mild operating conditions and low operating cost compared to various other separation processes such as evaporation, dialysis, ultracentrifugation, chemical precipitation, and the like. These advantages become especially critical when thermally unstable or biologically active materials are to be processed or when relatively large volumes of solvent are present in a solution to be processed.

Successful membrane-modulated separation processes depend, in major part, upon the characteristics of the membrane utilized. Among the desired characteristics are:

(1) High hydraulic permeability to solvent: The membrane must be capable of transmitting liquid at high rates per unit membrane area under modest pressures.

(2) Sharp "retention-cut-off": the membrane should be capable of retaining completely, or very nearly completely, all solutes of a molecular weight (or size) above some first specified value and of allowing the passage of all solutes of a molecular weight (or size) below some second value which should be as close as possible to the aforesaid first value.

(3) Good mechanical durability under the chemical and thermal conditions of service. Most preferably, a membrane should be suitable for use in a wide range of chemical and thermal environment.

(4) A minimum dependence of solvent permeability upon the type or concentration of solute.

(5) High fouling resistance.

To fulfill many of the above preferred criteria desirable for separation membranes, the so-called "anisotropic" membrane has been developed in recent years. (See, for example, U.S. Pat. Nos. 3,615,024; 3,526,588; 3,556,305; 3,541,005; and 3,549,016; all of which are hereby incorporated herein by reference to be generally illustrative of the types of anisotropic membranes contemplated and their method of use.) Briefly stated, the anisotropic membranes useful by this invention are fluid permeable materials characterized by unusually high hydraulic permeabilities through substantially permanent microscopic pores, surprising fouling resistance, excellent retention cutoff characteristics, and having excellent physical strength.

An anisotropic hollow fiber membrane is illustrated in FIG. 1 which is an radial crosssection of a single fiber 4. In the figure, the open channel or lumen 3 through which the liquid to be ultrafiltered is "normally" (but not invariably) passed is defined by a thin film or skin 1 which acts as the active membrane surface. The skin comprises a very thin barrier layer of fine pore material integral with a less dense support outer layer or sponge 2 which is much more porous and provides virtually no increase in resistance to hydraulic flow through the fiber. Various synthetic polymers are used to make the hollow fiber membranes. Unlike other ultrafiltration membranes, hollow fiber membranes are self-supporting, which allows the permeation of materials in either direction, i.e., from the lumen to the outside ("normal mode") or from the outside into the lumen ("backflush mode").

The dimensions of hollow fibers available vary greatly, depending largely on the intended type of separation, pressure drop, flow rates, materials to be separated, etc. For example, ultrafiltration (UF) fibers have lumen diameters of 0.008 inches up to 0.045 inches and higher whereas a common lumen diameter of 0.0016 inches may be employed for reverse osmosis. A typical anisotropic fiber may have a skin thickness of 0.001 mm. attached to a 0.1 mm. layer of open-celled sponge.

Due to the narrow inner channels of the fibers (lumen) liquids containing solute and/or colloidal materials pass through the channels at very high velocity, minimizing solute concentration at the membrane surface due to high shear forces and thereby avoiding blockage of the membrane pores.

In the application of hollow fibers to industrial processes, the fibers are typically combined into, e.g., bundles of 3,000, yielding 30 ft.$^2$ of membrane area. The bundles are inserted into cartridges with both ends rigidly secured in silicone rubber, epoxy or other suitable material. Individual cartridges are arranged in series or in parallel, with appropriate manifolds and pumps to make up custom built systems of desired capacity.

THE PRIOR ART

The concept of immobilizing a catalyst, in particular an enzyme, on hollow fibers is not novel; nor is the concept of performing enzymatic reactions with hollow fibers new. It has been taught that an enzyme may be encapsulated within the lumen of a hollow fiber by P. R. Rony, (*Biotechnology and Bio-engineering*, Vol. XIII, pp. 431–447 (1971)). Suggestions have even been made for immobilizing enzyme catalysts in the open-cell porous support structure (sponge) of an anisotropic hollow fiber membrane by soaking the fiber in a saturated solution of enzyme (L. R. Waterland, A. S. Michaels and C. R. Robertson, *A I Ch E Journal*, Vol. 20, No. 1, pp. 50–59 (1974)). A principal disadvantage of this latter technique (Waterland et al) is that it is operated under low transmembrane pressures to prevent rapid permeation of liquid from the lumen to the shell which would wash off enzyme from the sponge, reducing reaction kinetics appreciably.

Another investigator has suggested that an enzyme catalyst may be placed in the hollow fiber cartridge (outside of the fiber) to catalyze reaction (J. C. Davis, *Biotechnology and Bioengineering*, Vol. XVI, pp. 1113–1122 (1974)). Another example of work done to immobilize enzyme in the sponge layer and outside the fiber in free solution is: W. Lewis and S. Middleman, *A I Ch E Journal*, Vol. 20, No. 5, pp. 1012–14 (1974). Fiber entrapped enzymes have also been produced by spinning fibers with a spin dope containing enzymes (D. Dinelli and F. Marisi, *Enzyme Engineering*, Vol. 2 pp. 293–302 (1974)).

Unfortunately the relatively low reaction kinetics and/or inherent costs of each of the processes disclosed heretofore have inhibited their acceptance in commercial applications.

SUMMARY OF THE INVENTION

I have now discovered that catalyst may be immobilized in the sponge layer of an anistropic hollow fiber membrane in quantities far exceeding the loadings known heretofore, and have further developed novel processes by which substrate can be intimately contacted with the catalyst-loaded sponge layer to furnish high rates of reaction. The key to my discovery is the finding that a catalyst can be uniformly entrapped or immobilized in very high concentration in the sponge layer of an anistropic hollow fiber membrane when a solution or dispersion of such catalyst, preferably an enzyme, is caused to flow from the sponge side of the fiber into the lumen under pressure (backflush mode).

Unlike the prior art methods in which the enzyme was immobilized in the sponge layer of an anisotropic membrane (Waterland et al, supra) or in the shell side of a hollow fiber cartridge (e.g., Davis, supra) and contact between substrate and catalyst was effected by slow diffusion through the membrane wall, my method involves, as the driving force, positive flow of substrate through the immobilized enzyme on the sponge layer. Accordingly, by each of the variations to be explained hereafter there is a pressure differential ($\Delta P$) causing transport of the substrate to the enzyme and removal of product from the reaction zone.

BRIEF DESCRIPTION OF THE DRAWINGS

The invention will now be more fully explained with reference to FIGS. 1–8 appended hereto.

FIGS. 3–5 are axial sections of hollow fiber cartridges showing flow of liquids by the different alternative modes of operation.

Turning now to FIG. 2, tank 11 is an ordinary holding vessel for liquids to be circulated by pump 12. Hollow fiber reactor 13 is not unlike common hollow fiber ultrafiltration cartridges used heretofore for separation of liquids and solutes from larger molecules (fiber sizes greatly enlarged to aid description).

Figure 1:
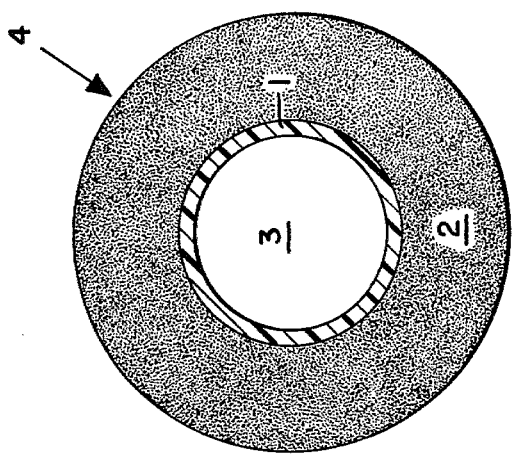
FIG. 1 is a radial cross section of a single hollow-fiber membrane (more fully explained above).

In order to load the sponge layer of hollow fibers 4 contained in reactor 13 with catalyst, a liquid solution or dispersion of such catalyst is first passed into tank 11 through line 25 with valve 23 open. The liquid used to dissolve or suspend catalyst must be extremely pure, such as a liquid previously ultrafiltered through the same fiber membranes of the reactor, to avoid blockage or contamination of the membranes. The catalyst-containing liquid is then circulated by pump 12 to the shell chamber 5 of reactor 13 through line 7 and valve 8 while valves 10, 15, 19 and 21 are closed. With valve 17 open the liquid from the catalyst-containing liquid supplied to the shell chamber 5 passes into and through the lumen of hollow fibers 4, into the manifold 24A and returns by way of line 16 to tank 11, having left essentially all active catalyst material immobilized in the sponge layer of the membranes. With regard to catalyst immobilization, it should be noted that the large catalyst molecules can pass easily into and through the large macropores of the sponge layer but will not pass through the microporous openings of the skin layer (see 2—FIG. 1, mentioned above) of the hollow membrane. Flow of the catalyst-containing liquid is continued for a minimum of one tank volume or until all enzyme is deposited. The tank is then cleaned and drained with valve 22 open.

In those instances where it is desirable to attach the catalyst more permanently to the membrane a crosslinking (coupling) agent such as gluturaldehyde may be recirculated through the reactor 13 following the same flow path as for the catalyst (supra). Again, care must be taken to use a "pure" (preferably ultrafiltered) liquid as the solvent or dispersant for the crosslinker to avoid fouling of the membranes.

There are three principal modes of operating the hollow fiber reactor in accordance with the invention, namely: (1) standard ultrafiltration mode, (2) backflushing mode and (3) recycling mode. For the purpose of clarity, the principal modes of operation will be explained hereinafter using $\beta$ galactosidase as the catalyst to convert lactose (a disaccharide), to glucose and galactose (monosaccharides).

(1) Standard Ultrafiltration Mode (UF Mode)

Figure 2:
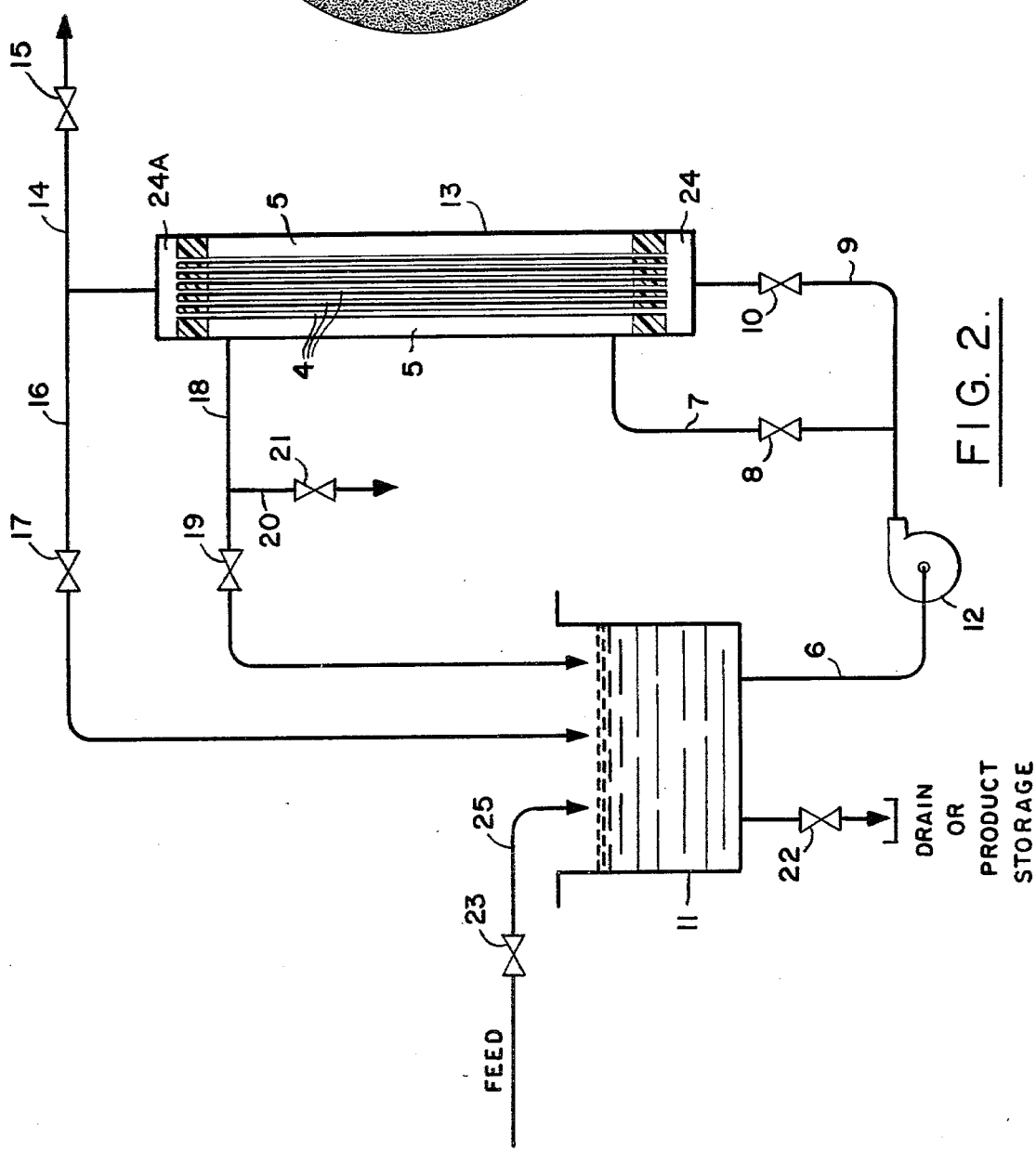
FIG. 2 is a line drawing of a composite catalytic reaction system that may be used to practice all the alternative modes of the method of my invention.

With the $\beta$ galactosidase attached to the sponge layers of the hollow fibers 4 of reactor 13, (see above method), lactose may be converted by the UF mode to glucose and galactose by enzymatic hydrolysis using the system shown in FIG. 2. By this mode (batch variation) tank 11 is loaded with an aqueous lactose solution (substrate solution) through valve 23 line 25. With all valves closed except valves 10, 17 and 19, pump 12 is used to circulate the lactose solution via line 9 and manifold 24 through the lumen of the fibers at a rate determined by the pressure drop across the cartridge, and then through valve 17, line 16 back to tank 11. Permeate, that is the liquid and lactose which pass through the hollow fiber membranes contacts the $\beta$ galactosidase whereupon the lactose is hydrolyzed to glucose and galactose, and thereafter the solution with the monosaccharides and any unreacted disaccharide leaves the shell 5 of the reactor 13 to return by line 19 to tank 11. By this batch UF mode recirculation of the solution from the tank 11 is continued until the desired conversion is obtained, whereafter product is recovered from the tank.

Employing the UF mode in continuous operation involves exactly the same initial steps as the batch operation except that after the desired conversion is achieved, either valve 15 or valve 21 is opened to continuously bleed out product while simultaneously feeding new substrate solution to tank 11 through valve 23. The choice of which valve to bleed product through depends upon whether it is desired that the product be ultrafiltered (through valve 21). Flow rates of new substrate and product bleed must be adjusted so that they are equal, and net residence time within the system is sufficient to maintain the desired conversion.

Of the three modes of reaction disclosed herein, only the standard UF mode presents any possibility that catalyst may be "washed" from the sponge layer into product (or permeate) due to the positive movement of material from the lumen through the membrane skin, the sponge and then through the cartridge shell. By actual experiments, it has been found, however, that a catalyst, when crosslinked within the sponge layer 2 will be more permanently fixed within the sponge layer and will resist being dislodged from the sponge layer, although there remains the possibility that some catalysts may resist crosslinking, and operation of the UF mode might result in dislodgement. Under such conditions, the other two alternative modes of operation may be preferable.

(2) Backflushing Mode (Catalyst already attached)

To practice the backflush mode, the tank 11 is initially loaded with a substrate solution made up with a pure liquid (preferably water ultrafiltered in a previous run of the system). For the "single pass" variation of the backflush mode, valves 8 and 15 are opened and all other valves are closed. Pump 12 is then used to circulate substrate liquid from the tank to the cartridge shell 5 where it passes through the membrane sponge (reaction) and skin into the lumen for transport out of the cartridge via line 14. The product stream leaving via line 14 may thereafter be subjected to a second stage of reaction, (if higher conversion is desired) further processed or used as formed. Continuous operation of the "single pass" backflush mode involves continually feeding substrate solution to the tank as product is removed through valve 15 (or the tank may be eliminated if a feed source is available upstream).

For batch operation of the backflush mode using recirculation of the permeate stream, valves 8 and 17 are opened with the other valves closed. Much like batch operation under the UF mode, the permeate is recirculated back to the tank 11, until the desired conversion is achieved.

For continuous operation (feed and bleed) of the backflush mode using recirculation of the permeate stream, the initial steps are identical with those recited immediately above for batch operation (backflush mode). Following initial conversion to the desired level (e.g., as measured at the tank), valves 23 and 15 are opened to begin continuous feed and bleed. Flow rates must be adjusted so that they are equal, and net residence time within the system is sufficient to maintain the desired conversion. Product containing glucose and galactose is removed for additional conversion, further processing or use through line 14.

It is important to note that product passing through the hollow fiber membranes by the backflush mode, the reverse of normal ultrafiltration, is nevertheless "purified" to the same extent as normal UF permeate. The same is true of one variation of the UF mode under continuous operation. Permeate quality product is, however, not produced by the recycling mode explained hereafter.

(3) Recycling Mode (catalyst already attached)

The tank 11 is loaded with substrate solution (not necessarily "pure") through line 25. With the sponge layer of fibers 4 loaded with β galactosidase by the method described above, valves 10 and 17 are opened and all others closed. Pump 12 is turned on to recirculate the substrate from the tank 11, through line 9, into the manifold 24, through the hollow fibers 4 and back to the tank 11 through line 16. Recirculation is continued until the desired conversion is obtained (batch variation).

As will be more fully explained hereafter, the recycling mode depends upon substantially differing transmembrane pressures along the length of the fiber to cause flow of substrate first from the lumen through the membrane and into the cartridge shell 5 (for reaction) and then flow of the product (with unreacted substrate) from the shell 5 back to the lumen.

To operate continuously (feed and bleed) under the recycling mode the initial steps are exactly as explained above for the batch variation. After the desired conversion is achieved, valves 23 and 15 are opened to feed and bleed, respectively. The feed of new substrate through valve 23 and removal of product through valve 15 must be adjusted so that they are equal and net residence time within the system is sufficient to maintain the desired conversion.

From time to time it will be desirable to clean the reactor 13 to remove fouled or spent catalyst (biological enzyme catalysts have limited active lives). By this invention cleaning is extremely quick and simple, providing the catalyst is not "permanently" fixed to the membrane sponge layer with a crosslinking agent or other bonding substance. The cleaning process normally requires only that a cleaning solution (caustic, acid or the like) be circulated through the system with valves 10, 17 and 19 open. The cleaning solution, therefore, passes through the membranes in the opposite flow direction used for the attachment of the catalyst.

Turning now to FIGS. 3-5, I will further explain the above-described three principal modes of operation with particular regard to the flow of substrate, substrate solution and product within the hollow fiber membrane reactor (cartridge).

The standard UF mode is illustrated in FIG. 3. In the figure substrate solution enters from line 9 into a space or manifold 24 at the bottom of the cartridge. The manifold prevents the substrate solution from passing into the cartridge shell 5 but allows passage of the solution into the lumen of the hollow fibers. Because of the constricted passageway and the positive pressure applied, the solution flows rapidly through the openings (lumen) in the hollow fibers to the upper manifold 24A, then out of the cartridge (reactor 13) through line 16. The outer shell 5 or chamber of the reactor 13 is an open space surrounding the bundle of hollow fibers and normally having a line 7 for passage of liquids into the shell 5 and line 18 for passage of materials out, with valves 8 and 19, respectively, on such lines.

By the UF mode the substrate solution with smaller molecules solubilized in the solution (including lactose) will pass through the membrane from the lumen to the shell, and in so doing, contact the spong layer of the membrane containing the β galactosidase. The lactose substrate will thereupon be converted to glucose and galactose. The flow of substrate solution permeating the membrane, optionally referred to herein as "permeate" after it passes through the membrane, is illustrated in FIG. 3, by the wavy arrows. Ultimately this permeate leaves the shell 5 through line 18 valve 19.

According to the backflushing mode (FIG. 4) lactose-containing solution is passed into the shell of reactor 13 with valves 10 and 19 closed. As the wavy lines illustrate, the solution containing the lactose permeates from the shell 5 to the lumen through the fiber membranes, then into the upper manifold 24A where it exits from the reactor through line 16 and valve 17. While permeating the membrane, the lactose contained in the solution is converted, at least partially, to glucose and galactose, and therefore the permeate leaving the reactor is richer in these monosaccharides than the lactose solution entering.

The recycling mode is illustrated in FIG. 5. Permeation of the hollow fibers by substrate solution takes place in two directions along the length of the fibers as shown by the wavy arrows. At the bottom of the reactor the lactose containing solution enters manifold 24, typically at a pressure of 25 psig, through line 9, valve 10, at its maximum reactor pressure, and thereafter passes through the lumen of fibers 4 to the upper manifold 24A maintained at a minimum pressure, typically 10 psig. The pressure in the shell when both inlet and outlet valves 8 and 19 are closed is intermediate between the inlet and outlet pressures and is approximately equal to the average of the inlet and outlet pressures in the hollow fibers 4. Thus the shell 5 pressure is less than the internal fiber pressure near the inlet manifold, causing permeation from the lumen to the shell, while the shell pressure is higher than the internal fiber pressure near the outlet causing permeation from the shell 5 into the fiber lumen. Said another way, the lactose passes out of the fiber lumen into the shell where it is converted by the catalyst to glucose and galactose which thereupon returns to the lumen. The unreacted lactose in passing back to the lumen undergoes further conversion. In the recycle mode, the shell 5 of the reactor 13, which is exposed to the catalyst in the sponge layer, can be maintained ultrapure, and sterile, which improves the life and performance of the catalyst.

Figure 6:
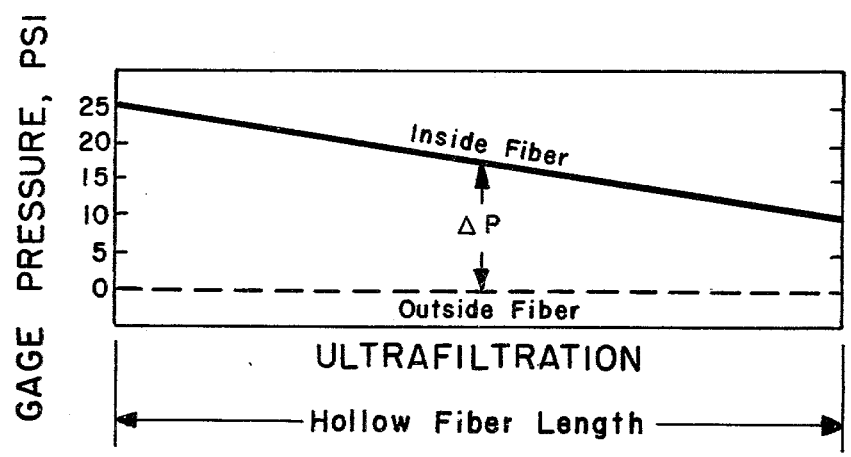
FIGS. 6–8 are pressure profile charts for the hollow fiber cartridges shown in FIGS. 3–5, respectively.
Figure 7:
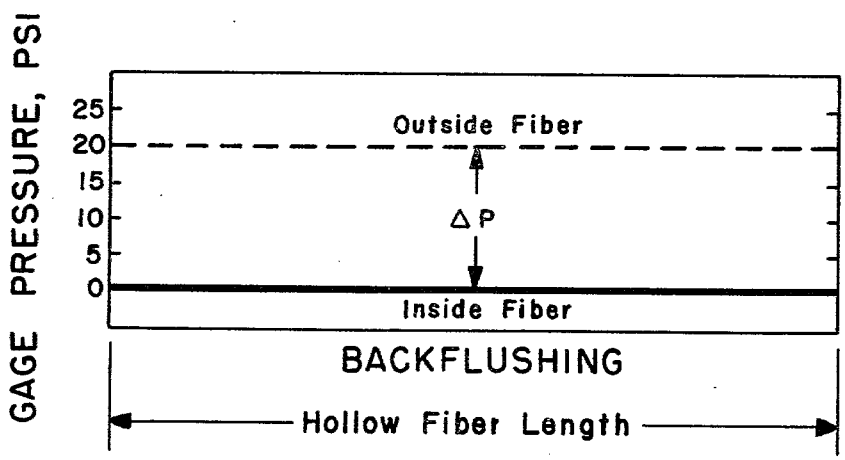
Figure 8:
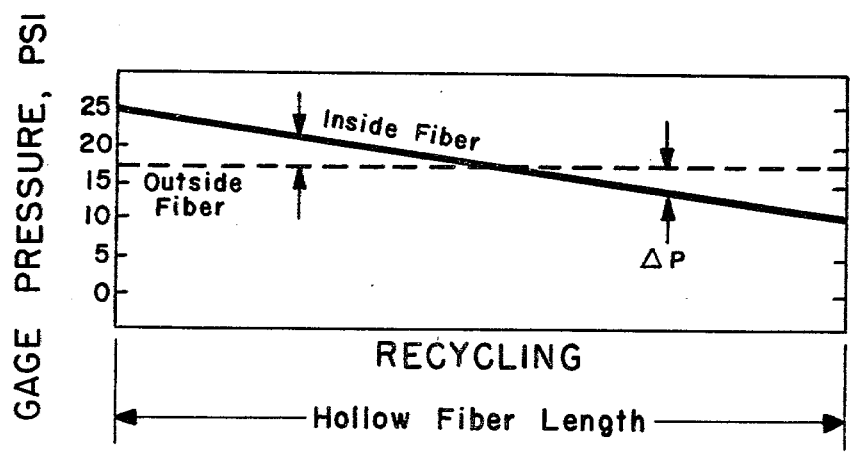

The pressure profiles in hollow fiber cartridges during the UF, backflushing and recycling modes are set forth in FIGS. 6-8. Positive pressure differences (fiber minus shell) result in flow from the inside of the fiber to the cartridge shell. Negative pressure differences result in flow from the cartridge shell to the inside of the fiber.

With regard to the standard UF mode, FIG. 6 shows that the inside fiber pressure, represented by the solid line, is always greater than the outside fiber pressure, represented by the dashed line, causing flow from the lumen to the shell over the entire length of the hollow fiber, with greater permeation corresponding to the greater $\Delta P$ near the inlet and corresponding lower permeation near the outlet.

The backflushing mode represented by FIG. 7 employs highest pressure on the outside of the fiber (shell) and lowest pressure on the inside of the fiber (lumen). Since the inside fiber pressure is constant over the entire length of the fiber, as is the shell pressure, uniform permeation takes place along the entire length of the fiber.

The recycling mode is operated at an inside fiber pressure which is greater than the shell pressure at the inlet and less than the shell pressure at the outlet, as shown in FIG. 8. Permeation of substrate solution is therefore greatest at the inlet, gradually decreasing to the center of length of the fiber and then reverse flow occurs for the remainder of the length of the fiber. It is important to the recycling mode therefore that there be a substantial $\Delta P$ over the length of the fiber to provide sufficient driving force in both directions to force substrate through the microscopic pores of the membrane in each direction.

A most significant aspect of the present invention is the finding that catalyst can be attached to the sponge layer of an anisotropic membrane at much larger concentrations than possible heretofore by the prior art method of soaking the fibers in catalyst (Waterland et al, supra) or filling the shell with a saturated solution of catalyst (Davis supra). With enzymatic catalysts, the rate of reaction is often directly dependent upon the concentration of enzyme according to the formula:

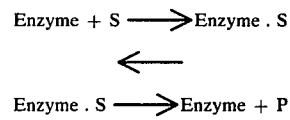

where S is substrate and P is product.

By backflushing the catalyst through the sponge layer, to attach it thereto, there is formed within the sponge, about the outside of the active membrane surface or skin, a highly concentrated boundary layer of catalyst. Although we do not intend to be bound to any theory herein for the practice of this invention, it appears that the concentrated catalyst layer on the sponge is in the form of a gel, much like the gel layer which forms by concentration of larger molecules at the inside skin of the membrane in ultrafiltration.

In addition to high concentration, the backflushing technique for attaching enzyme permits uniform deposition in the sponge layer. The reason for this is the uniform pressure gradient ($\Delta P$) across the membrane during operation in the backflushing mode (see FIG. 7). Uniformity maximizes substrate/catalyst contact thereby improving process efficiency.

By the nature of this process it is virtually impossible to precisely define the quantity of catalyst best suited for a particular reaction without experimenting with the desired mode of operation, pressure gradients, residence time in the enzyme zone, and the like. However, due to its physical containment in the shell side of the reactor, large excesses of catalyst may be used providing considerations of economy do not have overriding significance.

The present invention is applicable to catalytic reaction of chemical substances which (1) have molecular sizes sufficiently small to permeate the skin of an anisotropic membrane, (2) are soluble in substantial amounts in a liquid capable of permeation by ultrafiltration, and (3) are inert to the hollow fiber membrane. An additional requirement when operating under the backflushing mode and the recycling mode is that the product produced in the reaction also be sufficiently small in molecular size to permeate the membrane.

Suitable catalysts for use by the invention are those organic and inorganic substances capable of effecting reaction of the substrate and with at least sufficiently large molecular sizes not to permeate the membrane. Since the skin of the anisotropic membrane, the limiting membrane surface, normally contains micropores having openings between about 10 Å and 100 Å, the catalyst substances should either be particulate or have nominal molecular diameters at least equal to, and preferably greater than, the size of such openings. Generally, catalysts having molecular weights greater than 500 will not permeate the membrane, although lower molecular weight catalysts can be used by bonding, crosslinking or polymerizing with the fiber sponge.

The preferred chemicals which may be reacted by the method of the invention are proteins, carbohydrates, polysaccharides and the like. The preferred catalysts, therefore, are the enzymatic catalysts which are known in the prior art, such as discussed above. See also S. S. Gutcho, *Immobilized Enzymes, Preparation and Engineering Techniques,* Noyes Data Corporation, Park Ridge, N. J. (1974). A particularly preferred substrate is lactose (a carbohydrate), and lactase (β galactosidase) is the preferred catalyst therefor.

All enzymes, which are proteins, are theoretically retained by a hollow fiber membrane, providing the molecular weight cutoff of the membrane is low enough. Membranes with molecular weight cutoffs as low as 5000 are available commercially at the present, and even "tighter" fibers can be produced by known technology. Accordingly, all types of enzymes can be immobilized by the present invention. Some additional enzymes which may be immobilized by the present invention and which are useful in enzymatic catalysis are set forth below.

Amyloglucosidase (glucoamylase)

Used to produce glucose from starch, and in the brewing industry for the modification of the carbohydrate pattern after fermentation. This is done to sweeten the beer when desired.

This enzyme is one of the most important in use industrially as virtually all glucose is now prepared enzymatically.

Bacterial Amylase (alpha amylase)

Bacterial amylase hydrolyzes both starch and glycogen and oligosaccharides with at least 5 glucose units. The reaction products are glucose, maltose and oligosaccharides.
Uses:
(a) Starch liquefaction in paper industry
(b) Textile desizing
(c) Glucose production
(d) liquefaction of starch adjuncts in brewing mashes

Fungal Amylase (also alpha amylase)

Similar reactions to bacterial amylase. Principal uses in production of corn syrup (mixture of glucose, maltose and higher sugars). Also used in production of digestive aids in pharmaceutical industry.

Invertase

Catalyzes the hydrolysis of sucrose to D-glucose and D-fructose. Used in production of invert sugar.

Cellulase

Hydrolyzes cellulose to soluble polymers and D-glucose.

Glucose Oxidase

Converts glucose to gluconic acid.

Glucose Isomerase

Conversion of Aldo sugars into their respective Keto isomers such as D-glucose to D-fructose. The main use of glucose isomerase is in the production of isomerized syrups from glucose.

Isoamylase

Hydrolyzes starch and starch degradation products to maltose.

Tannase

Hydrolyzes tannic acid to lower molecular weight and soluble products. Tannic acid in foods have astringent and undesirable flavors which can be removed by this enzyme.

Galactose Oxidase

Catalyzes the oxidation of galactose to galactono-delta-lactone. This in turn mayy be used as a food grade acidulant.

In addition to the above enzyme catalysts, most of which are highly water soluble, water insoluble inorganic catalysts may also be used by the present invention. To illustrate, a nickel catalyst may be utilized by my method for dehydrogenation of a secondary alcohol, e.g., isopropanol, 2-butanol cyclohexanol, and 4-methylpentanol-2. A typical dehydrogenation reaction is:

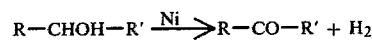

Various heterogenous catalyst which may be backflushed into the sponge layer of an anisotropic hollow fiber membrane to perform catalytic reactions are set forth in *Chemical Engineering Handbook,* Perry, 4th Edition, Ch. 4, page 12 et seq. (1963).

Anisotropic membranes are capable of withstanding the usually mild temperature conditions encountered in enzymatic catalysis and many reactions involving inorganic catalysts. Most commercially available membranes will withstand at least 50°–65° C., while more recently developed fibers will operate as high as 90° C. For higher temperature reactions, fibers have been spun from thermally resistant polymers (e.g., polyimides) to operate at 250° C. and higher.

The importance of hydraulic pressure as the driving force to accomplish contact between substrate and catalyst has been alluded to previously. Deficiencies in the prior art processes have largely been due to reliance upon concentration gradients to drive substrate molecules into contact with catalysts (diffusion). By the present invention operation of the reactor at pressures in the range of 1–100 psig is possible due to the outstanding strength of the anisotropic membrane, although pressures of about 5–25 psig are to be preferred for long life of the membranes. Transmembrane pressure drops ($\Delta P$) of at least 1.0 psig and preferably 5 to 25 psig are desirable to achieve high permeation rates and consequently high reaction rates.

Systems may be designed using multiple reactors in either series or parallel connection by this invention. Since the substrate solution may either be ultrafiltered (backflushing mode) or not (UF and recycling modes) while simultaneously being reacted, it may be desirable under some circumstances to combine two or more modes of operation in multiple stages of a processing system. The capability of performing "cold" sterilization by ultrafiltration of a solution passing through the hollow fibers makes the technique particularly suitable for food processing. Many other variations, some well known to the ultrafiltration art and others obvious from the foregoing disclosure will readily be conceived.

To further explain and illustrate the method of operation under the present invention I am presenting hereinafter several typical examples of catalytic reaction in anisotropic hollow fiber membrane catalytic reactors. These examples should be considered in no way limiting to the broader aspects of the invention which are explained elsewhere herein.

EXAMPLE 1

A catalytic batch reactor for enzymatic catalysis substantially in accordance with FIGS. 3-5 above was fabricated for the purpose of determining the feasibility of impregnating an enzyme on the spongy portion of an anisotropic membrane, as described above, and utilizing this enzyme to catalyze the conversion of lactose to glucose and galactose.

The study includes the use of three types of anisotropic hollow fibers, all available commercially from Romicon, Inc., Woburn, Mass., defined as follows.

1. Reactor A contained Romicon XM50 hollow fibers having a molecular weight cutoff of 50,000. This reactor would thereby retain in the sponge layer enzyme having a molecular weight in the general proximity of 50,000 or greater as well as a portion of the enzyme having a molecular weight lower than 500,000. The XM50 hollow fibers used in this reactor had a lumen diameter of 0.020 inches. The net membrane area of the reactor was 0.52 ft.$^2$ 2. Reactor B contained Romicon PM10 hollow fibers having a molecular weight cutoff of 10,000. This reactor would thereby retain in the sponge layer enzyme having a molecular weight in the general proximity of 10,000 or greater as well as a portion of the enzyme having a molecular weight lower than 10,000. The PM10 hollow fibers used in this reactor had a lumen diameter of 0.020 inches. The net membrane area of the reactor was 0.26 ft.$^2$ 3. Reactor C was essentially a duplicate of Reactor B described above.

All reactors were studies on a system such as that schematically described in FIG. 2. Each reactor was loaded with enzyme by backflushing 100 ml of a solution containing 0.1% lactase (from Wallerstein) having an activity of 202,000 activity units at a pH of 3.5. The net enzyme used in loading the fibers therefore was 0.1 gm.

The reactant solution, or feed solution, in all cases consisted of 200 ml of a 4.5% lactose solution. The net grams of lactose in the feed stream was therefore 9 grams and the net enzyme to substrate ratio was equal to 0.1 gm enzyme/9 gm lactose or 1.1%. Using these constant conditions, the performance of each of the reactors listed above is summarized below.

1. Reactor A, containing the 50,000 molecular weight cutoff fibers, was loaded with enzyme to a density of 0.19 gms of enzyme/ft$^2$ of membrane area. An aqueous solution containing 4.55 lactose was then backflushed through the reactor in the recirculating mode as described above. Conversion of lactose to glucose was monitored as a function of time. Results are listed below.

| Time, Minutes | Conversion, % |
|---|---|
| 0.0 | 0.0 |
| 4.0 | 4.4 |
| 10.8 | 5.0 |
| 20.0 | 5.3 |
| 30.0 | 5.5 |
| 60.0 | 9.2 |
| 90.0 | 11.0 |
| 979.0 | 32.9 |
| 1440.0 | 40.9 |

2. Reactor B, containing 10,000 molecular weight cutoff fibers, was loaded as described above. Because this reactor contained less membrane area, it loading density was increased to 0.38 gms of enzyme/ft$^2$ of membrane area. The enzyme was then crosslinked within the sponge layer by backflushing with a solution of glutaraldehyde. The reactor was then operated in the standard ultrafiltration mode with an aqueous solution of 4.5% lactose, batchwise with recirculation, and conversion of lactose to glucose monitored as a function of time. Results are listed below.

| Time, minutes | Conversion, % |
|---|---|
| 0.0 | 0.0 |
| 4.0 | 2.9 |
| 10.0 | 5.2 |
| 30.0 | 6.8 |
| 60.0 | 8.2 |
| 90.0 | 9.7 |
| 1220.0 | 74.7 |
| 1509.0 | 97.3 |

3. Reactor C was loaded as described above for Reactor B. The enzyme, however, was not crosslinked within the sponge layer as described in 2 above. The reactor nevertheless was operated in the standard ultrafiltration mode with a solution of 4.5% lactose, batchwise with recirculation, and conversion monitored as a function of time. Results are listed below.

| Time, minutes | Conversion, % |
|---|---|
| 0.0 | 0.0 |
| 6.0 | 2.4 |
| 10.0 | 2.6 |
| 29.0 | 3.6 |
| 60.0 | 4.8 |
| 110.0 | 6.7 |
| 1284.0 | 26.9 |
| 1465.0 | 30.2 |

The results listed above illustrate the important effect of enzyme concentration within the sponge layer as described elsewhere in this specification. The loading densities of the enzyme in Reactors B and C were equivalent at 0.38 gms enzyme/ft$^2$. However, the enzyme loaded on Reactor B was crosslinked within the sponge layer so that its density remained fixed at 0.38 gms per ft$^2$. The enzyme loaded on Reactor C was not crosslinked and hence was allowed to wash out of the sponge layer. Since both reactor systems were closed and were operated batchwise, the net enzyme concentration in grams enzyme per gram of substrate remained fixed (at 1.1%), but the enzyme concentration in the sponge layer of Reactor B, and hence the enzyme/substrate ratio in the sponge layer during operation of Reactor B was significantly greater, and remained greater, than that which existed in the sponge layer of Reactor C, and hence resulted in Reactor B giving a much higher conversion than Reactor C over comparable periods of time.

The conversion of Reactor B was furthermore significantly higher than that which was obtained by Reactor A in spite of the fact that the net enzyme used and net enzyme to substrate ratio was constant. This is further evidence of the importance of the enzyme loading density within the sponge layer with the enzyme loading density of Reactor B essentially twice that of Reactor A (0.38 gms/ft$^2$ as compared to 0.19 gms/ft$^2$). Note that one might conclude that Reactor A, having a much greater molecular weight cutoff than Reactor B (50,000 molecular weight cutoff as compared to 10,000 molecular weight cutoff) allowed the passage of enzyme during the enzyme loading operation, and hence had a lower enzyme density in the sponge layer than expected. That this in fact did not occur was determined by testing the process stream for enzyme activity, after loading the enzyme on the fiber, and finding it to be void of any activity. This is as would be expected since the molecular weight of the lactase used was reported to be greater than 130,000. Lowry analysis of the permeate stream did show the presence of protein, but this protein did not contain enzyme activity. In effect, the backflushing operation not only served to load the enzyme on the fiber, it also served to purify the enzyme (and thereby increase its possible net loading density).

The conditions under which the reactor systems described above were operated are summarized below.

|  | Reactors | | |
| --- | --- | --- | --- |
|  | A | B | C |
| Fibers | XM50 | PM10 | PM10 |
| Enzyme Loading Density gms/ft$^2$ | 0.19 | 0.38 | 0.38 |
| Enzyme Condition | not cross-linked | cross-linked | not cross-linked |
| Mode of Operation | Backflush | UF | UF |
| Operating Temp. °C. | 32 | 32 | 37 |
| $P_{in}$ psi | 15 | 25 | 25 |
| $P_{out}$ psi | 0 | 5 | 5 |
| Approx. Conversion after 1450 min. | 41.0 | 95.0 | 30.1 |

EXAMPLE 2

(Backflush Mode)

A catalytic batch reactor for enzymatic catalysis substantially in accordance with FIGS. 3–5 was fabricated and the reactor system performance was studied by operating in the single pass backflushing mode. In this example conversion, measured in terms of glucose production, was studied as a function of the number of passes through the fibers.

The reactor used contained Romicon XM50 hollow fibers having a lumen diameter of 0.045 inches. The molecular weight cutoff of these fibers is 50,000. This Reactor contained a net membrane area of 1.1 ft$^2$.

The reactor was loaded by backflushing 6 grams of lactase ($\beta$-galactosidase from Wallerstein) on to the sponge side of the XM50 hollow fibers. The net enzyme loading density was therefore 5.45 grams of enzyme/ft$^2$ of membrane area. A lactose solution, made up of permeate water at a concentration of 10% lactose was backflushed through the reactor. Conversion per pass, measured in terms of glucose production, was as follows:

| Passes | Conversion, % |
| --- | --- |
| 1 | 21.2 |
| 2 | 30.8 |
| 3 | 36.0 |
| 4 | 40.0 |

The rate of reaction here was significantly higher than that reported in Example 1 because of the increased loading density.

EXAMPLE 3

(Recycling Mode)

A reactor was prepared as described in Example 2. Its performance in the recycle mode was studied by recycling a 10% lactose solution through the lumen of the fibers with the shell ports closed. The lumen inlet and outlet pressures were held constant at 25 psig and 23.5 psig, respectively. This resulted in a shell pressure intermediate between 25 psig and 23.5 psig and hence an average transmembrane $\Delta P$ throughout the cartridge of less than 1 psig. This is an extremely low transmembrane pressure for feasible commercial operation, but is sufficiently high to demonstrate the sensitivity of this mode of operation. Conversion of lactose to glucose, monitored as a function of time, was as follows:

| Time, minutes | Conversion, % |
| --- | --- |
| 0 | 0 |
| 15 | 3.8 |
| 60 | 10.6 |
| 120 | 17.7 |
| 180 | 22.0 |

EXAMPLE 4

Using essentially the same mode of attaching the catalyst and processing the substrate solution as set forth above in Example 1 (backflushing mode—Reactor A) maltose is produced from starch with isoamalase serving as the catalyst immobilized in the sponge layer of the anisotropic hollow fiber membrane reactor.

EXAMPLE 5

Using essentially the same mode of attaching the catalyst and processing the substrate solution as set forth above in Example 1 (backflushing mode - with a polyimide fiber) acetone is produced by the dehydrogenation of isopropanol with a nickel catalyst serving as the dehydrogenation catalyst in the sponge layer of the anisotropic hollow fiber membrane. It is desirable to micronize the water-insoluble nickel catalyst and disperse it in ultrafiltered water together with surface-active agents under mild agitation prior to attachment to the sponge layer by the backflushing technique.

In general, catalyst densities of at least about 0.05 grams/ft.$^2$ of membrane surface area and as high as about 100 grams/ft.$^2$ are suitable, depending largely upon the reaction kinetics desired, limited, of course, by the characteristics of the particular catalyst for blocking the flow of permeate through the micropores of the membrane. Preferred catalyst densities are between 0.1 and 50.0 grams/ft.$^2$ while enzymatic catalysis is more preferably operated at densities of between about 0.1 and 30.0 grams/ft.² of membrane surface area.

By reference to the preceding examples it is readily seen that the present invention involves a heterogeneous catalytic system, that is, a system where the catalysts and reactants are not a single common phase. As such, the present invention differs from prior art enzyme catalytic systems wherein the reactants and enzymes are both solubilized in a simple homogeneous system, e.g., *Immobilized Enzymes*, O. R. Zaborsky, CRC Press, 1973, pp. 104–115. The differences between homogeneous and heterogeneous systems is fundamental.

Truly immobilized enzyme systems involve a solid support structure and, hence, are heterogeneous catalytic systems. In the case of homogeneous catalytic reactions such as those shown in the Zaborsky reference the reactions take place in solution, with or without the membrane.

One of the primary advantages of immobilized enzymes is that they are capable of repeated reuse and are readily removed from the reactors to stop the reaction. Thus, when a system needs to be cleaned or sanitized, the homogeneous system must be drained and the enzyme is lost. This normally has to occur at least once a day on any biologically active food processing stream.

Truly immobilized enzymes behave somewhat differently than they do in free solutions; sometimes the difference is positive and sometimes negative. One of the most important positive advantages for a heterogeneous system is increased stability, see, e.g., Enzyme Engineering, W. R. Vieth and K. Venkatasubramanian, Chemtech, May 1974, pp. 309.

It is well established that the rate of reaction in enzyme catalysis is often directly dependent on the concentration of enzyme. According to the present invention much higher loading density is possible than in a homogeneous system. For example, the density of enzyme in the sponge layer in the anisotropic membrane can be calculated for the preceding examples using the volume equations for the sponge layer as follows:

$$V = \pi/4 \, (D_o^2 - D_i^2) \, L$$

where V is the volume of the sponge layer, Do is the outside diameter of the fiber, Di is the inside diameter of the fiber and L is the length of the fiber. The dimensions of all of the fibers used herein are available from published literature of Romicon, Incorporated, Woburn, Mass.

With reference to Example 1, reactors A and B and Example 2, see above, the enzyme density produced by backflushing a 0.1% enzyme solution are as follows:

EXAMPLE 1

(a) 0.19 gms/ft² on the 20 mil ID XM50 fiber converts to 7.8 milligrams/milliliter in the sponge layer.

(b) 0.38 gms/ft² on the 20 mil ID PM10 fiber converts to 8.9 milligrams/milliliter in the sponge layer and,

EXAMPLE 2

5.45 gms/ft² on the 45 mil ID XM50 fiber converts to 95.0 milligrams/milliliter in the sponge layer.

Therefore, by loading enzyme into the fiber sponge layer to form a heterogeneous system, there has been a dramatic (95X in one case) localized increase in the concentration of enzyme. This is extremely significant with regard to the kinetics of enzyme catalysis and cannot be achieved by any of teh so-called "immobilized enzyme" systems of the prior art.

I claim:

1. A process for performing catalytic reactions utilizing an anisotropic hollow fiber membrane having a central opening or lumen radially surrounded by a continuous microporous skin layer serving as the active membrane and an outside macroporous sponge layer contiguous with the skin and serving to support the same, which comprises:
   (a) backflushing under hydraulic pressure a solution or dispersion containing catalyst molecules from the outside of the fiber membrane to the inside lumen to effect disposition of the catalyst molecules on the macroporous sponge layer, said catalyst molecules being selected from those too large to permeate the microporous openings in the skin layer;
   (b) applying hydraulic pressure to a solution containing a reactant substrate capable of undergoing reaction in the presence of the catalyst to force intimate contact between the reactant and the catalyst deposited in the sponge layer to form a product; and
   (c) removing under hydraulic pressure any unreacted reactant and the product from the sponge layer and recovering the same.

2. The process of claim 1 wherein the solution of reactant substrate is forced under hydraulic pressure of permeate from the lumen side of the anisotropic hollow fiber membrane to the sponge side where it is reacted in the presence of the catalyst.

3. The process of claim 2 wherein the solution of reactant substrate comprises predominantly water as the solvent and lactose is the reactant solute, and the catalyst is β galactosidase.

4. The process of claim 1 wherein the solution of reactant substrate is forced to permeate under hydraulic pressure from the sponge side of the anisotropic hollow fiber membrane, where it is reacted to the lumen side and the solution passing through the membrane contains product and any unreacted reactant substrate.

5. The process of claim 4 wherein the solution of reactant substrate comprises predominantly water as the solvent and lactose is the reactant solute, and the catalyst is β galactosidase.

6. The process of claim 1 wherein the solution of reactant substrate is first forced under hydraulic pressure to permeate from the lumen side of the anisotropic hollow fiber membrane to the sponge side where it is reacted initially in the presence of the catalyst to produce a product and thereafter the solution containing any unreacted reactant and the product permeates back into the lumen side of the fiber again contacting the catalyst in the sponge layer to further react any unreacted reactant contained in the solution.

7. The process of claim 6 wherein the solution of reactant substrate comprises predominantly water as the solvent and lactose is the reactant solute, and the catalyst is β galactosidase.

8. The process of claim 1 wherein the reactant is a carbohydrate and the catalyst is an enzyme catalyst capable of causing reaction of the carbohydrate.

9. The process of claim 1 wherein the catalytic molecules deposited on the sponge layer of the hollow fiber membrane are present in concentrations of at least about 0.05 g/ft.² of membrane surface area and up to about 100 g/ft.² of membrane surface area.

\* \* \* \* \*